(12) United States Patent
Weinberg

(10) Patent No.: US 6,872,178 B2
(45) Date of Patent: Mar. 29, 2005

(54) COLONOSCOPE APPARATUS AND METHOD

(76) Inventor: Andrew Mark Weinberg, 1650 Oakwood Dr., Unit E-304, Narberth, PA (US) 19072

( * ) Notice: Subject to any disclaimer, the term of this patent is extended or adjusted under 35 U.S.C. 154(b) by 152 days.

(21) Appl. No.: 10/298,786

(22) Filed: Nov. 18, 2002

(65) Prior Publication Data
US 2004/0097789 A1 May 20, 2004

(51) Int. Cl.$^7$ ................................................. A61B 1/00
(52) U.S. Cl. ...................................................... 600/114
(58) Field of Search ................................ 600/101–103, 600/109, 114, 139, 146, 149

(56) References Cited

U.S. PATENT DOCUMENTS 6,077,219 A * 6/2000 Viebach et al. ............. 600/114
6,679,833 B2 * 1/2004 Smith et al. ................. 600/114
6,726,675 B1 * 4/2004 Beyar ......................... 604/510
6,793,622 B2 * 9/2004 Konomura et al. ......... 600/152

FOREIGN PATENT DOCUMENTS

JP              5-115423       *  5/1993

* cited by examiner

Primary Examiner—Beverly M. Flanagan

(57) ABSTRACT

An improved colonoscope and method of removing or adding non-distal fluid from the colon during colonoscopy using a colonoscope. The colonoscope having at least a distal port and a non-distal port or plurality of non-distal ports to remove fluid from a shared channel within the colonoscope. Utilizing multiple ultrasound probes to determine a three dimensional image of anatomy behind the wall of a colon. Using microprocessors, motors to tighten/release wires of the colonoscope. Method of using an external joystick and a joystick on a handle of a colonoscope to effect navigation.

21 Claims, 5 Drawing Sheets

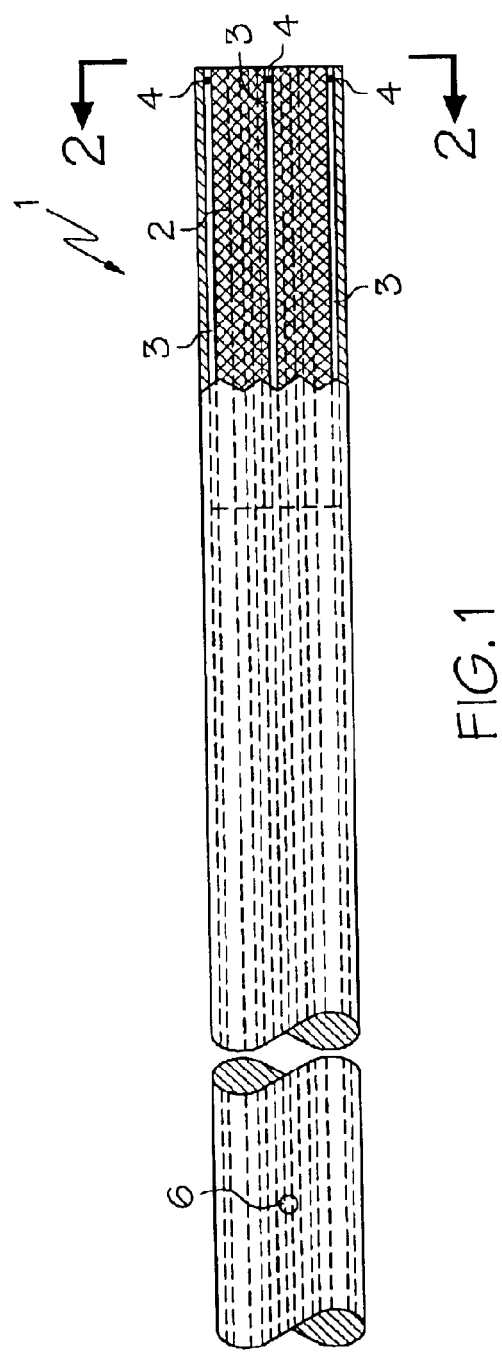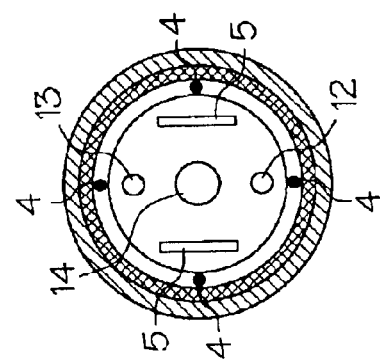

COLONOSCOPE APPARATUS AND METHOD

CROSS-REFERENCE TO RELATED APPLICATIONS

N/A

STATEMENT REGARDING FEDERALLY FUNDED RESEARCH AND DEVELOPMENT

N/A

REFERENCE TO SEQUENCE A LISTING, A TABLE, OR A COMPUTER PROGRAM LISTING APPENDIX

N/A

BACKGROUND

In colonoscopy procedures, air is introduced to distend the colon for advancement and navigation of the colonoscope. In addition, a distended colon is needed for proper visualization of possible growths. During colonoscopy, the air introduced can produce a sense of bloating and discomfort for the patient. Ultimately, air is removed by the distal end or tip of the colonoscope (which is generally the location of visual or other sensing equipment) or is passed out the rectum. Most air escapes during the procedure through the rectum but due to partial obstruction by the scope or colon anatomy, air is often trapped at various points along the colon. Currently patients in discomfort due to trapped air, can either remain that way for the remainder of the procedure, attempt to pass the gas on their own, or receive more medication. Additional medication for sedation increases the risk of respiratory depression of the patient and lengthens the recovery time for the patient. Therefore, a need exists for an improved colonoscope that reduces the amount of excess air which contributes to discomfort.

In addition, colonoscopy is currently performed manually directing and advancing a flexible tube through the colon. This technique is cumbersome and requires significant dexterity and training. In current designs, the scope often partially returns to a neutral position when the directional control dials are released. Control dials in current scopes usually employ control wires which are attached to the tip of the scope. These wires bend the tip of the scope when they are tightened. There is a need to partially automate the navigation of a colonoscope to be able to navigate tortuous colons, to safely increase the speed of the procedure, and reduce the amount of sedation required for the patient. Motorizing the advancement and positioning of a scope within the colon minimizes the risk of losing one's position during a procedure because the motors will hold the orientation even while the operator's hands are removed from the controls. In addition, tortuous colon anatomy can be navigated more precisely, with greater ease, and with less training. Finally, there is a procedure time benefit to have navigational assistance during scoping via computer interpreted ultrasound. Through automation of colonoscope advancement, retraction, torquing, and bending, this technology can easily be applied to other types of medical scoping procedures such as endoscopy, ERCP, bronchoscopy, trans-esophageal echocardiography, and nasopharyngoscopy.

SUMMARY

Applicants improved colonoscope and method reduces patient discomfort of colon distention by introducing one or more venting ports at locations other than the distal end of the colonoscope. This allows for greater reduction of unwanted air from within the colon during the procedure. Air that is not located near the tip where the camera is located is unwanted air because it increases patient discomfort and does not help with visualization. Further, providing colonoscope torque, advancement, and retraction motors—i.e. an external manipulating system for the colonoscope allows for utilizing an optional foot pedal controller (insertion or retraction of the scope if not incorporated in the external joystick control), microprocessors, and a joystick control. An optional foot pedal, a microprocessor, and an external joystick control allow the operator to advance, retract and torque the colonoscope with greater ease and precision than is conventionally possible. The external joystick can also be designed to incorporate forward and backward motions by pulling up on the stick to move backwards and pressing down the stick to move forward. In addition, a joystick knob is inserted into the handgrip portion of the colonoscope to effect the up, down, left, and right motions of the scope dials using just the thumb. Directional control by either joystick is effected by internal motors on the colonoscope directional knobs which rotate the knobs to effect tip orientation. Forward and backward motions can be controlled with a bi-directional button on the front of the scope handle next to standard air/water buttons. This is easier for individuals with small hands compared to reaching for the knobs of the colonoscope. A bi-directional button may also be placed just below the joystick knob on the handgrip to effect minor torque changes on the scope which are create side bending to the left and right. These new features now on the handgrip would allow complete freedom of the opposite hand which traditionally inserts and twists the scope as it is inserted into the colon. Therefore when a tool needs to be inserted into the colon which had traditionally required an assistant, the operator may be able to do that operation without assistance.

Today's scopes use directional knobs to tighten wires attached to the tip of the scope which in turn bend the scope in the desired direction. Motorizing the knobs in stead of manual operation allows for greater ease of operation and improved accuracy. A method of fluid manipulation comprising the steps of selecting a scope from the group consisting of an endoscope, bronchoscope, nasopharyngoscope, ERCP scope, transeophageal echocardiography scope, and a colonoscope. Providing said selected scope with at least one substantially non-distal port and providing said selected scope with a channel for fluid flow wherein the channel communicates with the at least one non-distal port as well as the standard distal port(s) on traditional scopes. A method of fluid manipulation within a colon comprising the steps of selecting a colonoscope and providing the colonoscope with at least one substantially non-distal port and a channel for fluid flow wherein the channel communicates with the at least one non-distal port. The fluid can flow into the channel and be directed out through one or all of the non-distal ports. Likewise, fluid from the colon can be drawn into one or all of the non-distal ports and directed out through the channel. A method of actuating a colonoscope tip comprising the steps of selecting a colonoscope, and providing a plurality of electric motors and wires that communicate with said colonoscope wherein said plurality of wires each having a first, second mode of operation, and wherein each said wires when actuated into said first mode tightens thereby exerting a force on said colonoscope tip. When each said wires are actuated into said second mode releases thereby not exerting a force on said colonoscope tip. A computer program analyses of ultrasound data from two ultrasound probes placed parallel to each other at the tip of a colonoscope creates a three dimensional image from the axial (not radial) data of the anatomy behind a lumen. This imaging provides for greater clarity than two dimensional ultrasound. A colonoscope comprising a body portion and a channel within the body portion. Two ultrasound sensors and a distal port are located at a distal end of the body portion, and at least one substantially non-distal port also exists. A colonoscope comprising a distal port located on a body portion of the colonoscope, and a channel for directing fluid and an optional attachment portion that attaches to the main body of the colonoscope.

BRIEF DESCRIPTION OF THE DRAWINGS

Further aspects of the instant invention will be more readily appreciated upon review of the detailed description included below when taken in conjunction with the accompanying drawings, of which:

FIG. 1 shows a partially disassembled colonoscope tip side view Showing a flexible mesh, tip actuating wires, weld points, and a non distal port.

FIG. 2 shows an end view of a colonoscope tip with a light source, camera, distal port, anchor points for directional wires, and two ultrasound probes.

DETAILED DESCRIPTION AND THE PREFERRED EMBODIMENT

Figure 5A:
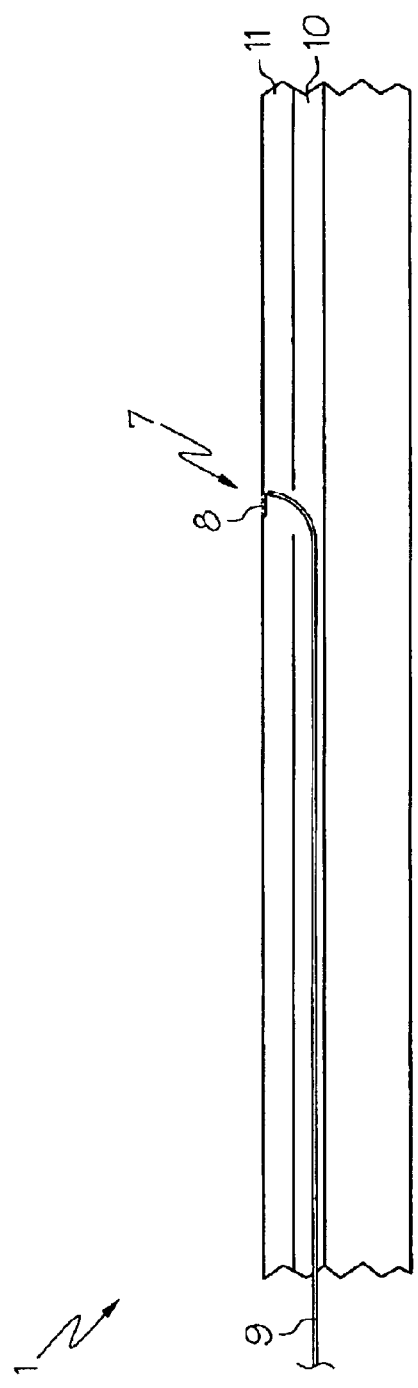
FIG. 5A shows a side view of a colonoscope with a resilient elastic non-distal port cover in a closed position, a fluid channel with which the port cover communicates with, and an actuating wire attached to the port cover.
Figure 5B:
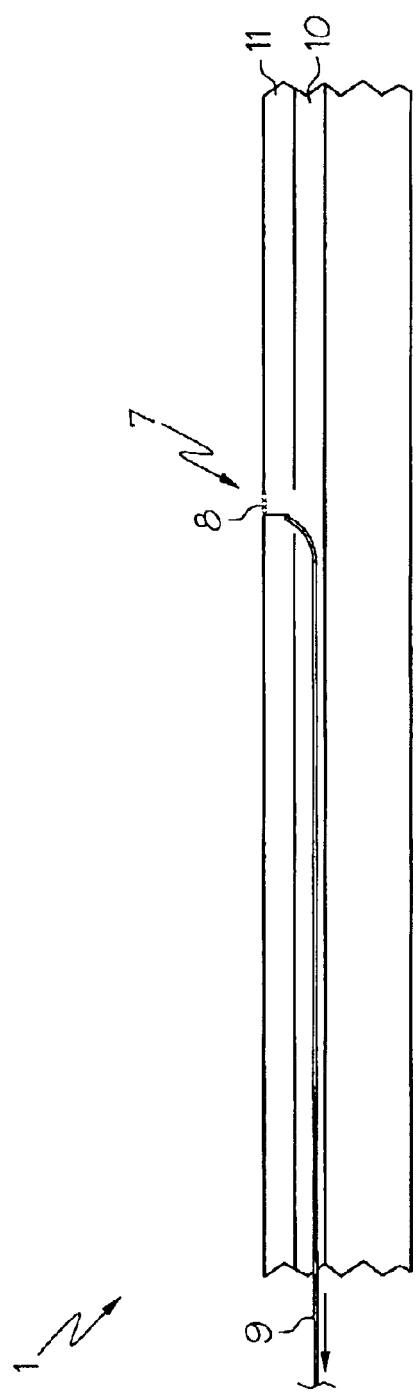
FIG. 5B shows a side view of a colonoscope with a resilient elastic non-distal port cover in an open position, a fluid channel with which the port cover communicates with, and an actuating wire attached to the port cover.
Figure 7:
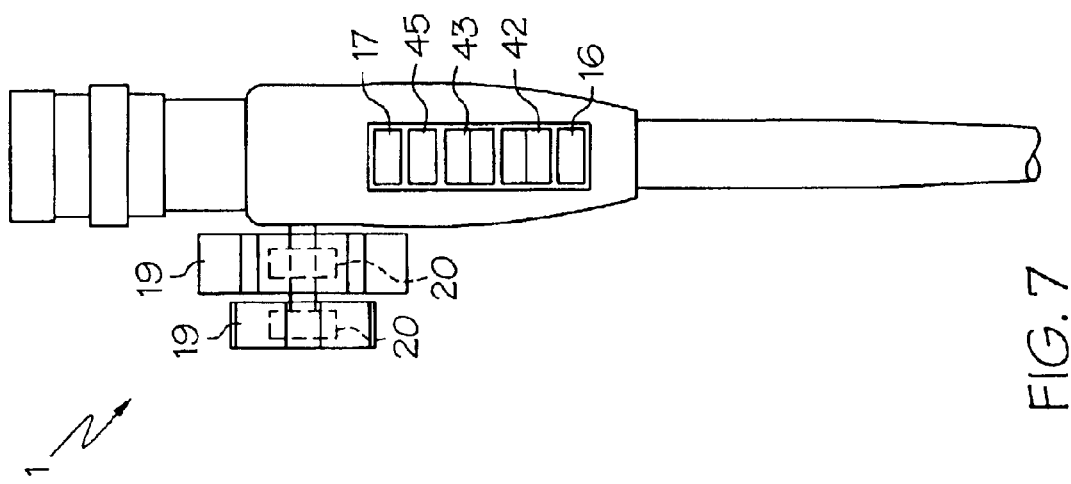
FIG. 7 shows a front view of the colonoscope handle and directional control dials and button controls.
Figure 6:
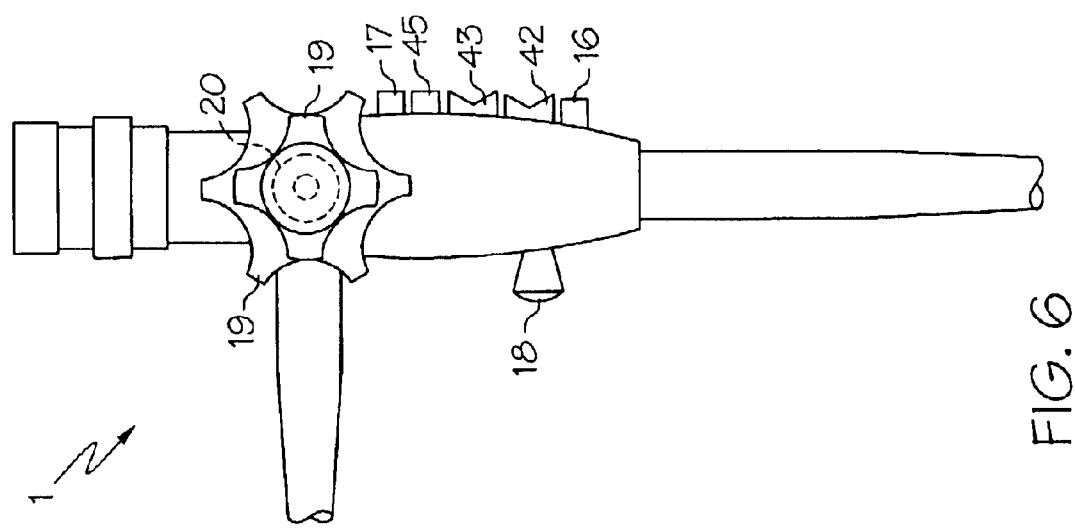
FIG. 6 shows a side view of the colonoscope handle with navigation dials, associated internal navigation dial motors, and a directional joystick button.

Applicants improved colonoscope and method reduces patient discomfort of colon distention by introducing one or more non-distal ports 6 at locations other than the distal end (colonoscope tip) as shown in FIG. 1 of scope 1. The proximal portion of the scope 1 is defined as the portion that is near the rectum when the scope 1 is substantially inserted into the rectum. The non-distal portion in this invention refers to the mid-region of the scope 1. Proximal (near the rectum) air is likely to be voided through the rectum by the patient while distal air (away from the rectum and hence near the distal tip of the scope) is moved toward the rectum by peristalsis or is suctioned by the traditional port 12 shown in FIG. 2 at the distal end of scope 1. This device will enable air removal at various locations from the rectum to the mid colon depending upon how much of the scope 1 is inserted. Beside air, other fluid such as medications, colon lubricant or water could be inserted or removed at various rates through channel 11 by adjusting the amount resilient non-distal port cover 7 FIG. 5 is opened by actuator button 16 connected to actuator wire 9 FIG. 6. Actuator wire 9 travels in a separate channel 10 FIG. 5. Both non-distal port 6 and distal port 12 communicate and draw fluid through channel 11. Non distal port 6 has a low friction screen 8 made of nylon (fine surgical steel or other non porous low friction materials would also be acceptable) covering the opening of non distal port 6 to avoid inadvertent trapping of mucosa during suctioning FIGS. 5A and 5B. The greater non-distal port actuator button 16 is depressed, the more flow through channel 11. Thus variable flow through non-distal port 6 and channel 11 can be controlled according to the patient's and doctor's needs. Distal port 12 and non distal port 6 can be independently actuated by distal port button 17 and non-distal port button 16 respectively FIG. 6 and FIG. 7. Distal port 12 has a standard port cover (not shown) that is routinely closed unless actuated by button 17. Fluid is suctioned into channel 11 when either button is partially depressed and fluid is inserted into the channel and out through the respective port when the respective button is fully depressed. In the fully depressed mode of the buttons (16,17), the respective port opens and fluid is inserted. Fluid insertion or suction is provided by air/fluid/video/ultrasound source 36. Applicants improved colonoscope and method also increases patient comfort during the procedure as well as speeds the procedure by not having to provide additional medication to the patient due to over distension of the bowel. By using less anesthesia, medication risk to the patient and recovery time are minimized. It is possible that more patients will be able to be seen due to shorter recovery time and that procedure time will be modestly shortened due to increased patient compliance and comfort.

FIG. 1 shows a colonoscope 1 having a flexible mesh 2 of nylon or surgical grade wire under the exterior surface of the colonoscope 1 which has been removed for visualization. The flexible mesh 2 is located only near the tip and is used to increase tip flexibility. The colonoscope body 1 is made of industry standard flexible plastic with low friction external surfaces. Typically, four wires 3 provide for direction wire control and are attached by welding the wires 3 to the colonoscope 1 at wire anchor points 4 FIG. 2. The wire anchor points 4 are located ninety degrees apart and are used to actuate the colonoscope tip during operation. It should be understood that an attachment to a conventional colonoscope could be added that would have non-distal ports 6. A wire 3 is tightened or loosened from bi-directional dial motors 20 connected to directional dials 19 FIG. 6. As the dial 19 is rotated, it tightens one wire 3 and loosens the opposing wire 3. There are two dials; one for up down and one for left right navigation. In manual mode, the dials are rotated by hand as in current technology. This invention incorporates joystick control 21 and handle joystick 18 to orient the scope in the desired direction.

In addition, a fully automated navigation system may be used. The operator actuates the colonoscope tip up, down, left, or right by manipulating the external joystick 21 forward (up), backward (down), left (left), and right (right). The joystick 21 also actuates the navigation mechanism 34 comprised of torque mechanism 29, and advancement mechanism 22. The joystick may be rotated clockwise or counterclockwise to effect respective torque and associated minor amount of desired side bending on the scope. By use of navigation apparatus 34 which communicates with computer 38 and joystick 21, scope advancement, retraction, and torque is controlled. By depressing joystick 21, the scope 1 is advanced and by gently pulling up on joystick 21, the scope is withdrawn. Joystick 21 also actuates four primary directions by communication with computer 38 and bi-directional dial motors 20 on scope 1 FIG. 7 and FIG. 8. The dial motors 20 turn dials 19 which tighten or loosen directional wires 3 attached to the scope tip at anchor points 4. This action causes a specific orientation of the tip of the scope. The joystick 21 may actuate any combination of the four primary directions, advancement/retraction, or torque simultaneously with proportional magnitude except opposing directions. For instance, several movements may be accomplished at once by twisting the joystick (torque), moving it to the left and forward with one motion of the hand. This ability allows great precision and is faster than only being able to use one motion at a time. Thus all navigation is semi automated by the joystick control 21. Tip direction is controlled by actuating dials 19 manually or by actuating the bi-directional dial motors 20 FIG. 7 with the external joystick 21 or handle joystick 18 FIG. 6. When dials 19 are used manually, the computer places dial motors 20 in neutral and if the scope body is manipulated manually, the computer 38 places the torque motors 32 and advancement motors 27 in neutral allowing manual orientation of the scope.

An external manipulation device 34 capable of advancement, retraction, and torque motions to said colonoscope via control inputs from joystick 21 or by handle joystick 18. Handle joystick 18 is a short knob similar to that seen on some laptop computers. The thumb can be placed comfortably on top of the joystick to actuate up/down and left/right motions. On the front of the handle of the scope, two position buttons are used; advancement button 42 for advancement/retraction/neutral and the torque button, 43, for clockwise/counterclockwise/neutral torque FIG. 9. Both buttons have variable intensity and speed capability and may be used simultaneously with the other joystick controls. The use of auxiliary joystick 21 is optional and depends on user preference compared to handle joystick 18. All motions including torque and advancement are incorporated onto joystick 21, but when handle joystick 18 is used, torque and advancement are controlled by separate buttons on the scope handle.

Figure 4:
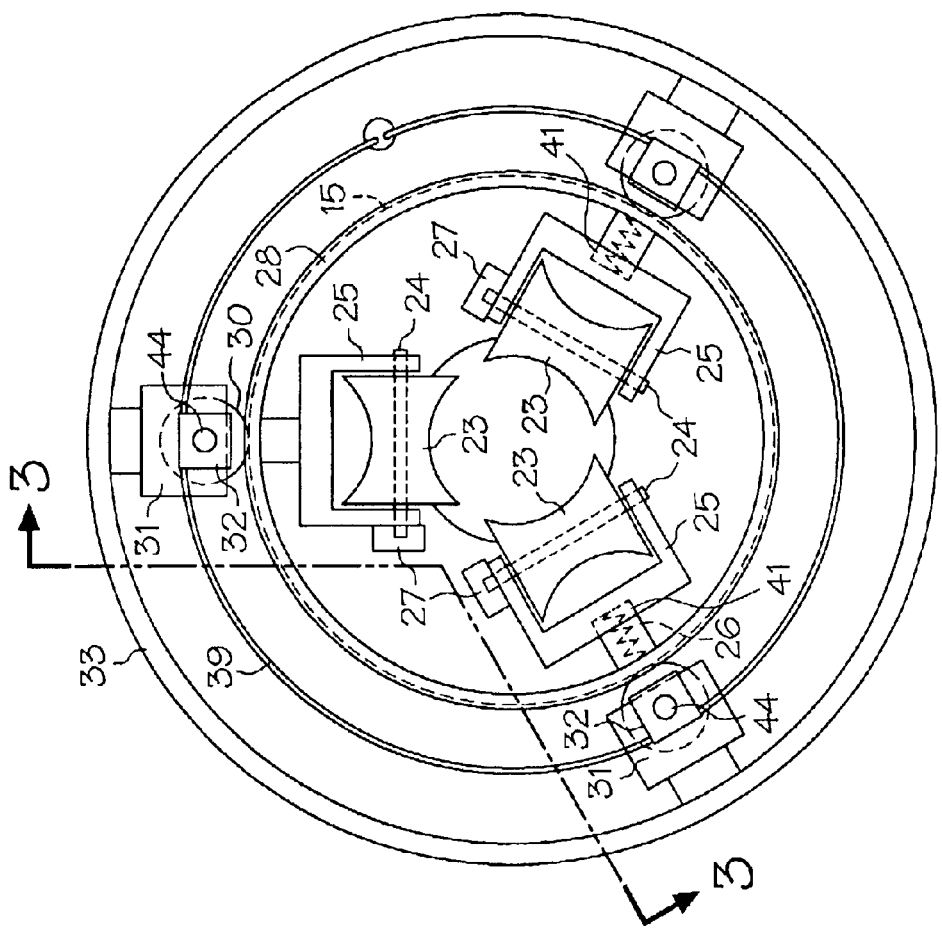
FIG. 4 shows a cutaway front view of a navigation device without its front cover, comprised of an advancement/retraction device through which a colonoscope is inserted and a torque device which houses the advancement device.
Figure 3:
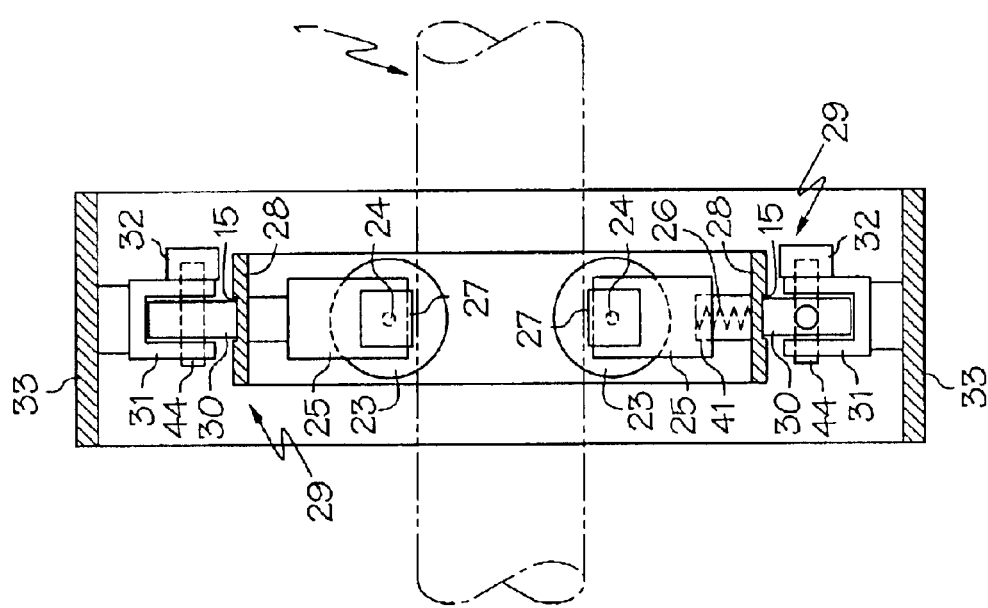
FIG. 3 shows a side view of a colonoscope portion inserted through a cutaway view of navigation device.

The navigation apparatus 34 comprising an advancement/retraction mechanism 22 is surrounded by a torque device 29 FIG. 3 and FIG. 4. The colonoscope tip is inserted into the advancement apparatus 22 and is engaged by rollers 23. The advancement apparatus comprises roller 23, roller axle 24, roller mount 25, roller mount spring 26, roller bi-directional motor 27, and inner casing 28. The rollers 23 have a compressible high traction synthetic rubber surface and are designed to curve around the scope. In addition, the rollers 23 are oriented 120 degrees apart to facilitate even stress on the colonoscope and have a gap between each to allow for scope lubricant to be pushed out of the way. This spacing between each roller helps avoid slippage between the colonoscope 1 and rollers 23. Although lubricant is applied to the scope distal to the navigation mechanism during insertion, if the scope is withdrawn during the procedure, some lubricant will enter the rollers. Sufficient pressure is exerted by rollers 23 to overcome slippage, but the pressure is designed not to adversely compress the scope. Two of the rollers 23 incorporate a spring 26 to allow engagement of various diameter scopes as well as the change in diameter along the length of each individual scope. A third roller 23 does not incorporate a spring so it may facilitate a firm foundation for the other rollers to push against. The rollers 23 are connected by roller axle 24 and the axle is fastened onto mount 25. Each roller 23 is driven by a synchronized motor 27. When roller 23 is compressed to engage a scope 1, spring 26 compresses to allow mount 25 to further engage channel 41 FIG. 4. Mount 25 includes a peg portion that attaches to inner casing 28 and it is the peg portion that further engages channel 41 when spring 26 is compressed. There are removable front and back faceplates 46 shown on FIG. 9. The front faceplate is removed for viewing in FIG. 4. The advancement motors 27 actuate four modes; forward motion, reverse motion, fixed position, or neutral free rotation. Neutral (free movement) is automatically selected by computer 38 to facilitate scope adjustment relative to the navigation mechanism or for manual adjustment using the directional dials 19 whenever the dials are manually rotated or the scope is manually inserted/removed or torqued. The computer senses intended manual use by a force that exceeds user input parameters to any of the individual motors in the invention. Thus, the action of turning a directional knob momentarilly applies a force to the dial motors and as the force exceeds a user predetermined maximum value, the corresponding motor is disengaged allowing neutral mode. Motor control automatically resumes after a user specified time input to computer 38 is exceeded since the most recent triggering force for manual mode. The advance/retraction mechanism 22 is enclosed by inner casing 28. The inner casing 28 has a groove 15 FIG. 3 on its outer surface to contain torque rollers 30 and maintain proper orientation by the torque apparatus 29. The inner casing 28 is shaped as a donut with the rollers 23 protruding on the inner diameter to engage scope 1. The motors 27 and electrical wiring 39 are tightly sealed to allow direct immersion in cleaning solution after use. Both inner casing 28 and outer casing 33 although water tight, are designed to dissipate unwanted heat build up during operation.

Torque mechanism 29 contains bi-directional torque motors 32, torque rollers 30, torque roller mount 31, and outer casing 33. The torque apparatus 29 rotates advancement mechanism 22 counterclockwise or clockwise to effect the same rotation on the colonoscope 1. Torque rollers 30 are made of a compressible synthetic rubber that facilitates removal of the advancement mechanism groove 15 on the inner casing by compressing the surfaces of the rollers. The torque rollers also have excellent traction ability with respect to the advancement mechanism casing 28. No springs are needed in the torque mechanism. Torque on scope 1 induces minor side bending of scope 1 where clockwise torque creates right side bending and counterclockwise torque creates left side bending. Torque motors 32 control torque rollers 30 which ride in the groove of the outer surface of inner casing 28. The entire torque mechanism 29 is never in contact with bodily fluids and does not need to be cleaned internally. However, the casing is watertight and the entire navigation apparatus 34 may be immersed in solution for cleaning after use. User specified maximum torque and directional forces may be controlled by the computer to minimize risk to scope damage, patient injury or patient discomfort.

An additional feature of the present invention is the ability to obtain three dimensional viewing of anatomy behind the lumen wall. This feature includes ultrasound probes 5, camera, 14, light source 13, computer (ultrasound processor, video processor, controller) 38, power source 35, video and ultrasound monitor 37, electrical connecting wires 39. Two ultrasound probes 5 placed parallel at the tip of the scope for axial, not radial data collection (FIG. 2) provide a three dimensional view. They are oriented for longitudinal (axial), not radial viewing. In addition, light source 13 provides illumination for camera 14. The data from the ultrasound probes are analyzed by computer 38. The computer combines data from both ultrasound probes 5 when the probes rest against the lumen wall to assemble a three dimensional picture and displays the image on video monitor 37 next to the camera video feed on the same monitor 37.

Figure 8:
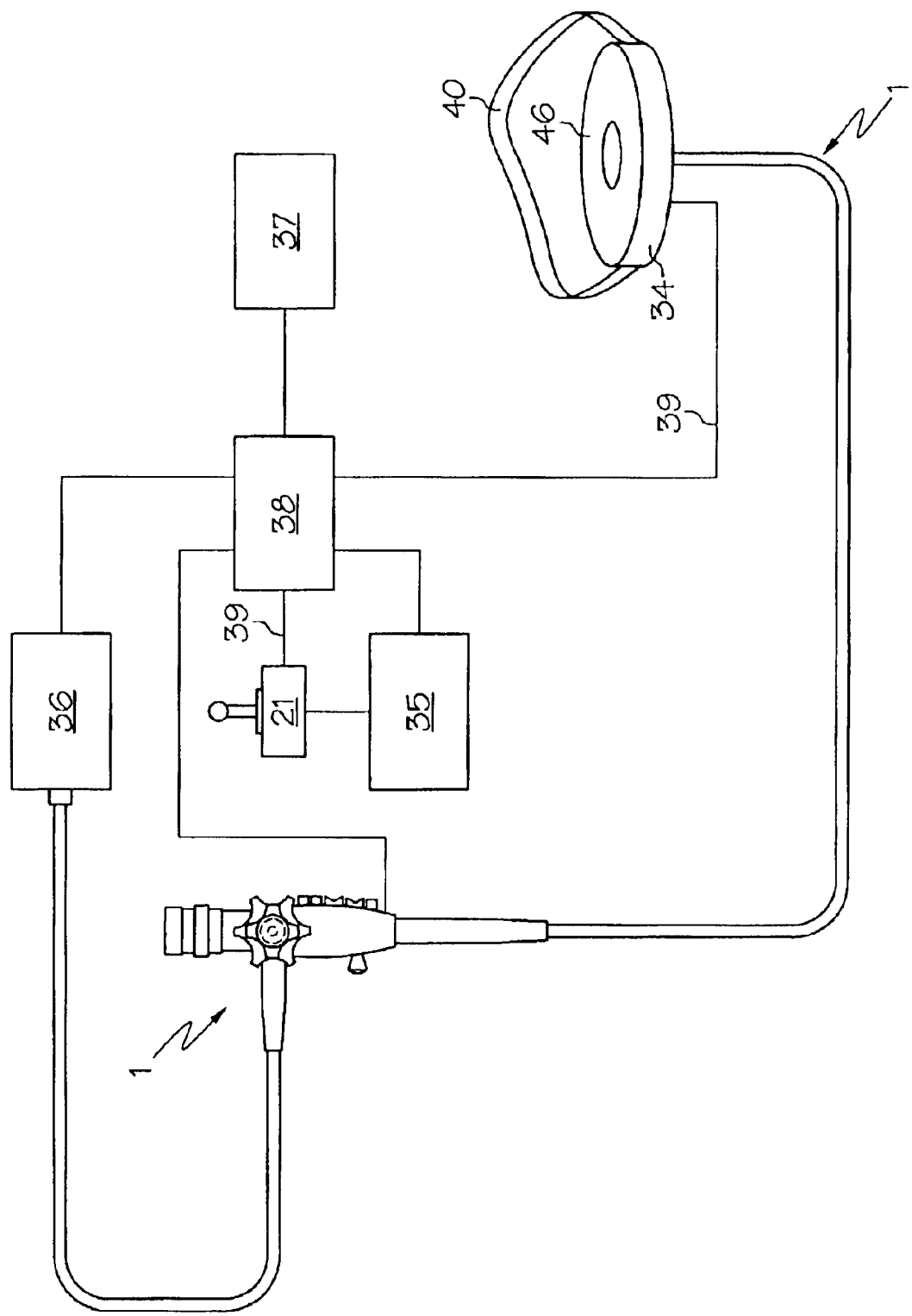
FIG. 8 shows the overall view of the apparatus comprising a colonoscope inserted through a navigation device, controlled by an external joystick, or a hand controller on the scope, computer, power source, video/air/water source, a fastening belt, and connecting electrical wiring.

FIG. 8 shows the overall invention. A person would lie on their side and the navigation device 34 would be placed proximal to the rectum. A belt 40 attached to casing 33 of the navigation device 34 is then placed around the abdomen of the patient to secure the device relative to the patient. The leather belt may be made of any other suitable material such as cloth, or spandex that facilitates ease of use. Although only one navigation device 34 is shown, it is understood that a plurality of navigation devices could be used in series on the scope and controlled by computer 38 to provide extra traction and control.

Although the invention has been described in detail in the foregoing embodiments, it is to be understood that they have been provided for the purposes of illustration only and that other variations both in form and detail can be made thereupon by those skilled in the art without departing from the spirit and scope of the invention, which is defined solely by the appended claims.

What is claimed is:

1. An apparatus for navigating a colonoscope comprising:
   a torque mechanism capable of clockwise and/or counterclockwise rotation, and
   an advancement mechanism;
   said advancement mechanism having a colonoscope insertion port, and
   motors, and
   rollers, and
   wherein said advancement mechanism has a plurality of mounts that fixedly attach to secure the apparatus during an operation.
2. An apparatus for navigating a colonoscope comprising:
   a torque mechanism, and
   an advancement mechanism,
   said advancement mechanism having a colonoscope insertion port, and
   motors, and
   rollers, and
   wherein said advancement mechanism has a plurality of mounts that fixedly attach to secure the apparatus during an operation, and
   wherein at least one of said mounts contains a spring, and
   wherein said spring is capable of allowing at least one of said mounts to engage various diameter colonoscopes at the colonoscope insertion port.
3. An apparatus for navigating a colonoscope comprising:
   a torgue mechanism, and
   an advancement mechanism,
   said advancement mechanism having a plurality of mounts that fixedly attach to secure the apparatus during an operation, and
   wherein said advancement apparatus is surrounded by said torque mechanism and said torque mechanism is comprised of mounts, rollers, motors, and a shell, and wherein said torque apparatus is capable of torquing the advancement apparatus which engages said colonoscope.
4. The apparatus of claim 3 wherein the outer shell of the torque mechanism attaches to a belt worn by a patient thereby aligning the colonoscope port with said patient's rectum.
5. An advancement device encased by an inner shell with a groove on the outer surface of said inner shell,
   wherein said advancement device is surrounded by a torquing mechanism comprising:
   a torquing mechanism encased in a shell, and
   an advancement device comprising a plurality of rollers, a plurality of roller mounts, and a plurality of bi-directional motors which cooperate to advance or retract a colonoscope with respect to a colon in a synchronous fashion;
   wherein an inner casing is rotated by torquing torque rollers that engage a groove on the external surface of the inner casing, bi-directional torque motors, supported by torque roller mounts; and
   wherein the torquing mechanism rotates an inner advancement mechanism which rotates the colonoscope.
6. An advancement device encased by an inner shell with a groove on the outer surface of said inner shell,
   wherein said advancement device is surrounded by a torquing mechanism comprising:
   a torquing mechanism encased in a shell, and
   an advancement device comprising a plurality of rollers, a plurality of roller mounts, and a plurality of bi-directional motors which cooperate to advance or retract a colonoscope with respect to a colon in a synchronous fashion;
   wherein an inner casing is rotated by torquing torque rollers that engage a groove on the external surface of the inner casing, bi-directional torque motors, supported by torque roller mounts; and
   wherein the torquing mechanism rotates an inner advancement mechanism which rotates the colonoscope; and wherein the shell is attached to a belt worn by a patient thereby aligning the colonoscope with a patient's rectum.
7. An advancement device encased by an inner shell with a groove on the outer surface of said inner shell,
   wherein said advancement device is surrounded by a torquing mechanism comprising:
   a torquing mechanism encased in a shell, and
   an advancement device comprising a plurality of rollers, a plurality of roller mounts, and a plurality of bi-directional motors which cooperate to advance or retract a colonoscope with respect to a colon in a synchronous fashion;
   wherein an inner casing is rotated by torquing torque rollers that engage a groove on the external surface of the inner casing, bi-directional torque rollers, supported by torque roller mounts; and
   wherein the torquing mechanism rotates and inner advancement mechanism which rotates the colonoscope, and
   wherein a plurality of shells provide support for a colonoscope.
8. The advancement device of claim 7 wherein one of a plurality of shells is attached to a belt worn by a patient and another of a plurality of shells is aligned with said one shell thereby aligning the colonoscope with said patient rectum.
9. A method of maintaining a colonoscope centered within the colon comprising the steps of:

selecting a colonoscope, and providing a plurality of roller mounts, and providing a plurality of rollers capable of rotating a colonoscope clockwise and/or counterclockwise, and providing said colonoscope with a computer, and providing said colonoscope with two parallel placed ultrasound probes, video sensor, and providing communication between said ultrasound probes and said computer, and wherein when said ultrasound probes are in contact with the wall of the colon, a computer program analyzes sensor inputs as data to compute a three dimensional ultrasound image of the anatomy behind the wall of the colon.

10. The method of claim 9 wherein said computer is a microprocessor.

11. The method of claim 9 wherein said ultrasound probes and video sensor are placed near the colonoscope tip, and said ultrasound probes are oriented parallel to each other, and said ultrasound probes are oriented for axial data collection.

12. The method of claim 9 further comprising the steps of:

providing a joystick control that controls said colonoscope advancement, retraction, torque, and sidebending along said plurality of rollers.

13. The method of claim 12 where said joystick control interacts with bi-directional dial motors on said scope to control the orientation of said scope.

14. The method of claim 13 further comprising a torque button and an advancement/retraction button on said colonoscope handle which control a navigation mechanism external to said colonoscope.

15. The method of claim 9 further comprising the steps of:

providing a joystick control on said colonoscope that controls colonoscope sidebending to create up, down, left, and right movements of said scope tip.

16. The method of claim 15 further comprising the steps of said joystick controlling directional control wires that position the tip of a colonoscope.

17. A method of actuating a colonoscope tip comprising the steps of:

selecting a colonoscope, and providing a plurality of electric motors that communicate with said colonoscope, and providing a plurality of wires that facilitate communication between said plurality of motors and said colonoscope, and wherein said plurality of wires each having a first and second mode of operation, and wherein each of said wires when actuated into said first mode tightens, thereby exerting a force on said colonoscope tip, and wherein each of said wires when actuated into said second mode releases thereby not exerting a force on said colonoscope tip;

providing said colonoscope with a computer, and providing said colonoscope with two ultrasound probes, video sensor, and providing communication between said probes and said computer;

providing communication between the plurality of motors and said computer, and providing a plurality of roller mounts, capable of clockwise and/or counterclockwise rotation, and providing a plurality of rollers for moving the colonoscope.

18. A method of claim 17 further comprising the step of:

providing an external motor means for providing torque, advancement and retraction to the colonoscope.

19. The method of claim 18 wherein said joystick control cooperates with said wires to control orientation of a colonoscope tip.

20. The method of claim 17 further comprising the steps of:

providing a joystick control and providing advancement, retraction, torque, and side bending of said colonoscope along said plurality of rollers by said joystick control.

21. A method of claim 17 wherein means to fix the position of the colonoscope do not require an operators contact.

* * * * *